United States Patent [19]

Wiegand

[11] 3,960,941

[45] June 1, 1976

[54] 3-HYDROXY-3,4-DICARBAMOYLBUTYRIC ACID AND SALTS

[75] Inventor: Karl E. Wiegand, Baton Rouge, La.

[73] Assignee: Ethyl Corporation, Richmond, Va.

[22] Filed: Jan. 20, 1975

[21] Appl. No.: 542,347

Related U.S. Application Data

[62] Division of Ser. No. 347,822, April 4, 1973, Pat. No. 3,911,002, which is a division of Ser. No. 172,627, Aug. 18, 1971, Pat. No. 3,769,337.

[52] U.S. Cl. .............................. 260/534 E; 260/315
[51] Int. Cl.$^2$......................................... C07C 101/24
[58] Field of Search .................................. 260/534 E

[56] References Cited
OTHER PUBLICATIONS

Migydichian, Org. Synthesis, vol. 1, pp. 370 and 426, 1957.
Wilcox et al., "J. Am. Chem. Soc.," vol. 72, (1950), pp. 5019–5024.
Suh et al., "J. Pharm. Sciences," vol. 60, (1971), pp. 930–933.

Primary Examiner—Joseph E. Evans
Attorney, Agent, or Firm—Donald L. Johnson; John F. Sieberth; Shelton B. McAnelly

[57] ABSTRACT

It is disclosed that citric acid or its salts are obtained by the hydrolysis of a 3-carbamoyl-3-hydroxy-4-cyanobutyric acid or salt, that a 3-carbamoyl-3-hydroxy-4-cyanobutyric acid or salt is obtained from a 3-carbamoyl-3,4-epoxybutyric acid or salt, that a 3-carbamoyl-3,4-epoxybutyric acid or salt is obtained from a 3-carbamoyl-3-hydroxy-4-halobutyric acid or salt, that a 3-carbamoyl-3-hydroxy-4-halobutyric acid is obtained from a 3-cyano-3-hydroxy-4-halobutyric acid or salt, that a 3-cyano-3-hydroxy-4-halobutyric acid or salt is obtained from a 3-oxo-4-halobutyric acid or salt, that a 3-oxo-4-halobutyric acid or salt is obtained from a 3-oxo-4-halobutyryl halide, and that a 3-oxo-4-halobutyryl halide is obtained from diketene. Preferred halide compounds are compounds of chlorine.

5 Claims, 10 Drawing Figures

3-HYDROXY-3,4-DICARBAMOYLBUTYRIC ACID AND SALTS

CROSS-REFERENCE TO RELATED APPLICATION

This application is a division of application Ser. No. 347,822, filed Apr. 4, 1973, now U.S. Pat. No. 3,911,002, which in turn is a division of application Ser. No. 172,627, filed Aug. 18, 1971, now U.S. Pat. No. 3,769,337.

BACKGROUND OF THE INVENTION

1. Field of the Invention

The invention relates to the preparation of citric acid and of salts of citric acid.

2. Description of the Prior Art

Citric acid or its salts are useful in different ways as exemplified by the following patents: as a plasticizer, U.S. Pat. No. 2,409,703; as a bleaching agent, U.S. Pat. No. 2,529,831; as a food antioxidant, U.S. Pat. No. 2,563,855; as a detergent component, U.S. Pat. No. 2,765,280.

The principal prior sources of citric acid and its derivatives are recovery from natural products such as citrus fruits and production via micological or fermentation processes. The recovery of citric acid from natural products or sources is disclosed in U.S. Pat. Nos. 2,027,264; 2,193,904; and 2,396,115. The production of citric acid by micological processes is disclosed in U.S. Pat. Nos. 2,353,771; 2,739,923; 2,883,329 and 3,335,067.

Heretofore the chemical synthesis of citric acid or of its salts has proved to be very difficult. In fact, the only known U.S. Pat. relating to a chemical synthesis of citric acid is No. 3,356,721 which issued in 1967 and there is nothing in the patent to show that a significant yield of citric acid or its salts is obtained with the process described therein. Since the amount of natural source citric acid is limited, there has been a need in the art for a commercially attractive chemical synthesis process for producing citric acid or its salts.

OBJECTS

It is an object of the present invention to provide a process for synthesizing citric acid and salts of citric acid from readily available moderate cost raw materials.

Another object of the present invention is to provide process operations for producing compositions which are useful intermediates for the synthesis of citric acid and salts of citric acid.

Another object of the present invention is to provide a process for producing intermediate compositions that can be hydrolyzed to produce citric acid or its salts in high yield.

Another object of the present invention is to provide a process for producing the intermediate compositions of the preceding object via the cyanide cleavage of the epoxy group of a 3-carbamoyl-3,4-epoxybutyric acid or a salt or ester thereof to form 3-carbamoyl-3-hydroxy-4-cyanobutyric acid, or a salt or ester thereof.

Another object of the present invention is to provide a process for producing 3-carbamoyl-3,4-epoxybutyric acid or a salt or ester thereof from a 3-carbamoyl-3-hydroxy-4-halobutyric acid, or a salt or ester thereof.

Another object of the present invention is to provide a process for producing a 3-carbamoyl-3-hydroxy-4-halobutyric acid or a salt or ester thereof from a 3-cyano-3-hydroxy-4-halobutyric acid or a salt or ester thereof.

Another object of the present invention is to provide a process for producing a 3-cyano-3-hydroxy-4-halobutyric acid or a salt or ester thereof from a 3-oxo-4-halobutyric acid or a salt or ester thereof.

Another object of the present invention is to provide a process for producing 3-oxo-4-halobutyric acid by a water hydrolysis of a 3-oxo-4-halobutyrylhalide.

Other and further objects and features of the present invention will become apparent upon a careful consideration of the following discussion and the accompanying drawings.

SUMMARY OF THE INVENTION

Figures 1, 2:
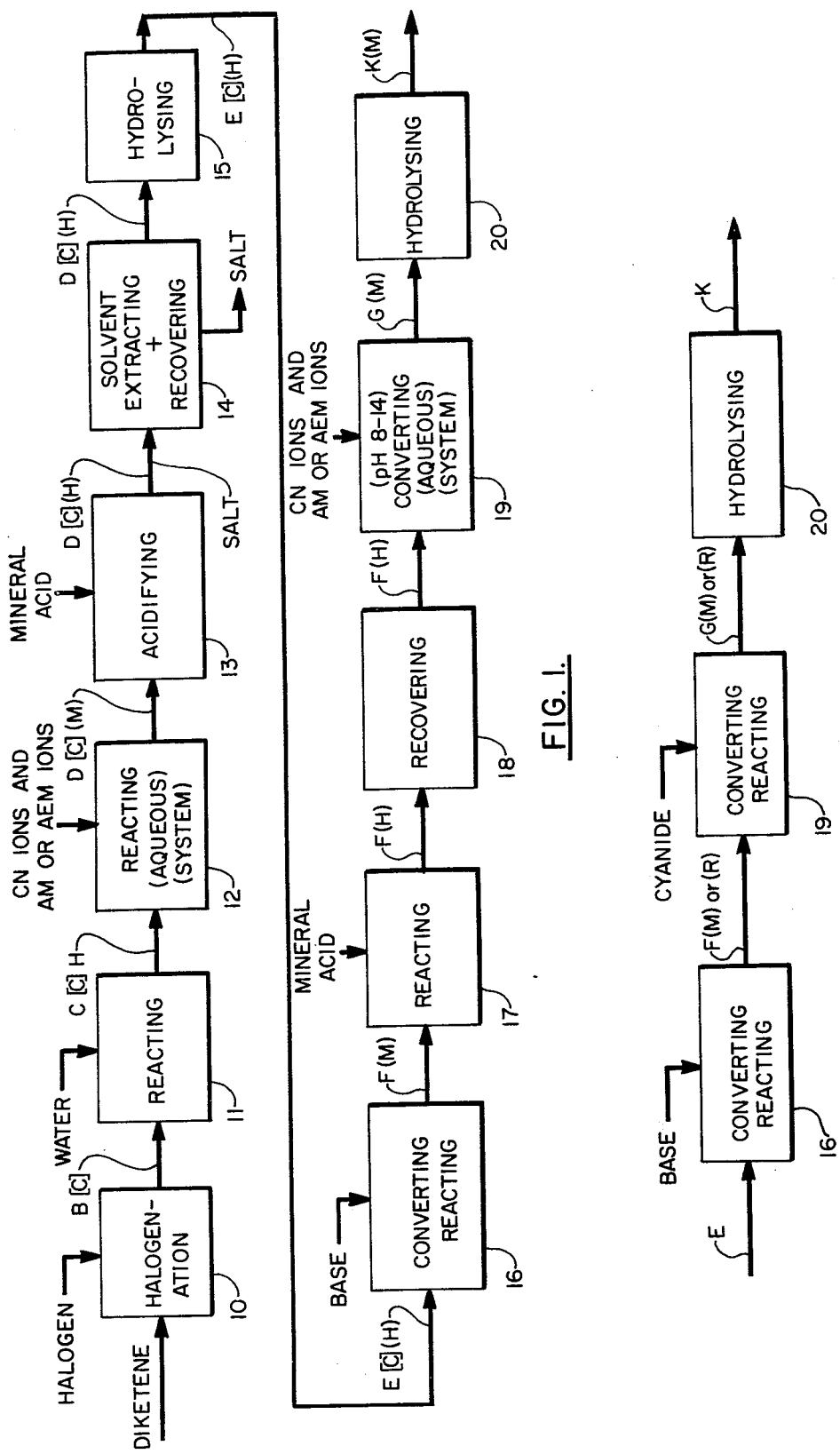
FIG. 1 shows in block form a preferred embodiment of the features of the present invention whereby citric acid or its salts or esters are produced from diketene via a sequence involving several novel reactions which provide preferred ways to produce and utilize the several intermediate compositions involved in the overall process.
FIG. 2 shows a portion of the process of FIG. 1 whereby a particularly useful intermediate composition; viz, 3-carbamoyl-3-hydroxy-4-halobutyric acid, or a salt or ester thereof is converted to citric acid or a salt thereof by three process steps involving (1) epoxidation with halogen elimination of a 3-carbamoyl-3-hydroxy-4-halobutyric acid to form a 3-carbamoyl-3,4-epoxybutyric acid derivative. (2) cyanide scission of the epoxy group of the 3-carbamoyl-3,4-epoxybutyric acid derivative to form a 3-carbamoyl-3-hydroxy-4-cyanobutyric acid derivative and (3) hydrolysis of the 3-carbamoyl-3-hydroxy-4-cyanobutyric acid derivative to produce citric acid or a salt thereof.

The present invention provides, inter alia, a method of producing citric acid and its salts from 3-oxo-4-halobutyryl halide.

In accordance with one embodiment of this invention 3-oxo-4-halobutyryl halide, which may be readily formed by halogenation of diketene, is hydrolyzed to produce 3-oxo-4-halobutyric acid which is reacted with hydrogen cyanide to produce 3-cyano-3-hydroxy-4-halobutyric acid. If metal ions are present in the system in which this cyanide reaction is performed so that a salt of 3-cyano-3-hydroxy-4-halobutyric acid is or tends to be formed, the system is preferably acidified to convert any such salt to the corresponding free acid before performing the next reaction, viz. hydrolysis. On hydrolysis, the 3-cyano-3-hydroxy-4-halobutyric acid produces 3-carbamoyl-3-hydroxy-4-halobutyric acid which readily eliminates halogen when placed in a basic system to form a 3-carbamoyl-3,4-epoxybutyric acid salt. The 3-carbamoyl-3,4-epoxybutyric acid salt is treated with cyanide to cause cleavage of the epoxy ring thereby forming a 3-carbamoyl-3-hydroxy-4-cyanobutyric acid salt which on hydrolysis in acid or basic media yields citric acid or salts of citric acid depending on whether acidic or basic conditions are employed in the hydrolysis operation.

The foregoing process sequence may be represented by the following series of equations:

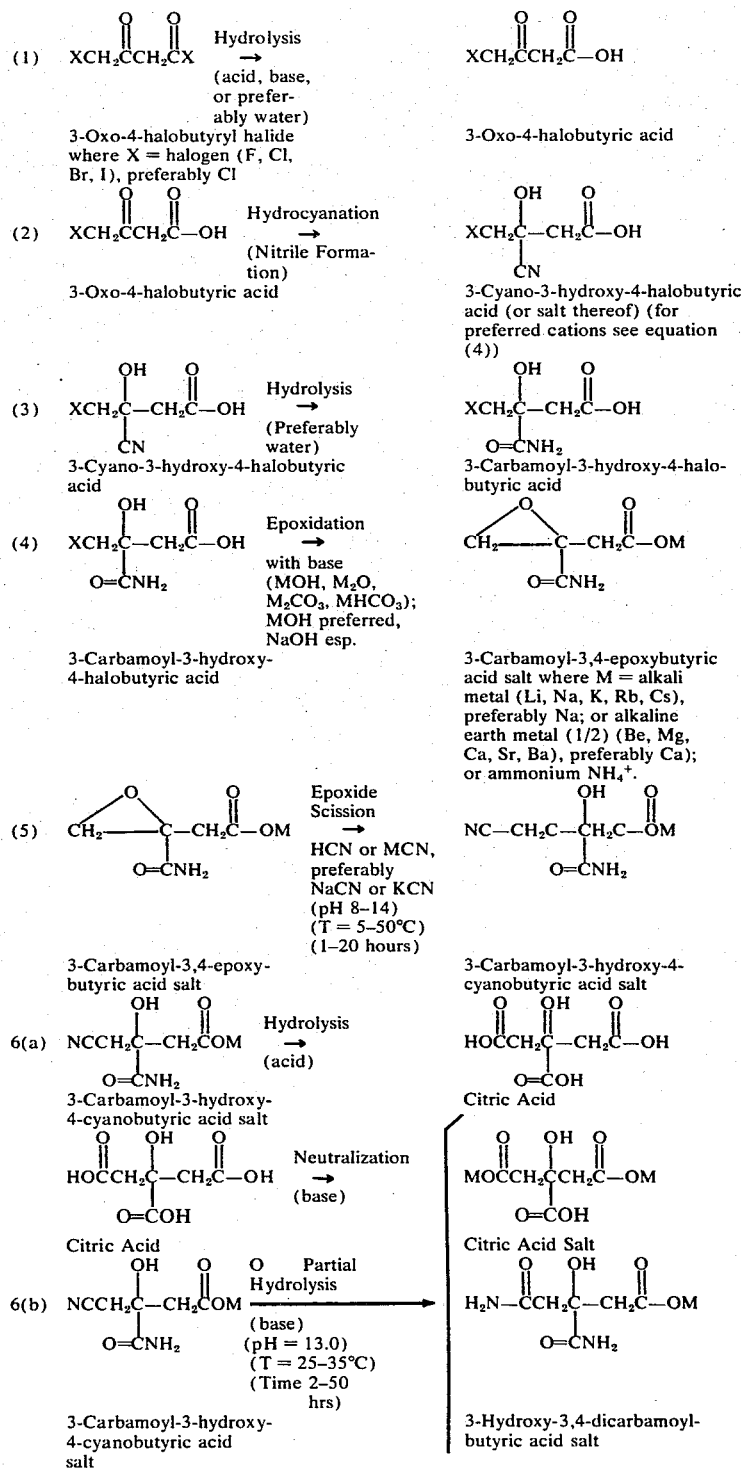

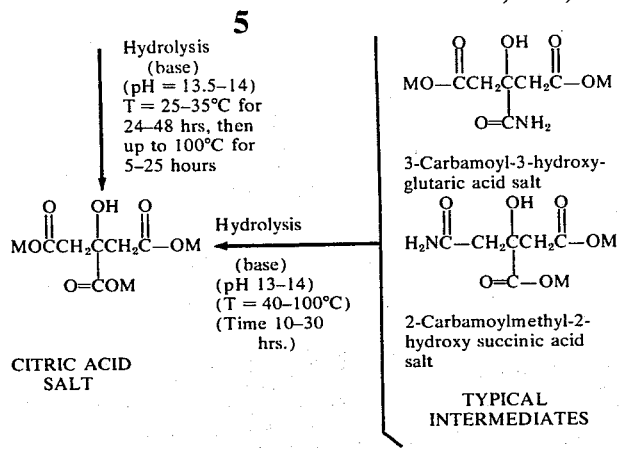

CITRIC ACID SALT

TYPICAL INTERMEDIATES

The foregoing process is subject to numerous variations. Thus although the reactions are preferably conducted in an aqueous environment or in aqueous solution, it is possible to employ suitable anhydrous organic reaction media including protic solvents in some of these reactions. Conversions between the acid and salt forms provide ways to enhance purification and by-product removal as well as to provide stable intermediates for storage or more convenient transportation to subsequent processing. Also in some instances, the use as reactants of esters rather than acids or salts facilitates handling and the selection of solvent systems. Thus, the fundamental processing steps discussed may be supplemented by form changing steps (i.e., neutralizations, saponifications, esterifications, ester hydrolysis etc.), purification steps, drying steps or the like. Further, although the process is most preferably conducted on a continuous basis in an unbroken sequence, it is feasible to perform the process on a batch or semi-batch basis and also to interrupt the processing sequence operations, e.g. by storing or transporting intermediates for subsequent use in the succeeding process steps. In addition, in many instances several of the reactions described may be conducted concurrently or sequentially in a single environment to appear as a single processing step, while single reactions may be conducted in a staged manner to appear as several processing steps.

Inasmuch as this process is subject to numerous variations, the following are some of the process embodiments disclosed or provided by this invention.

A. Converting 3-carbamoyl-3-hydroxy-4-halobutyric acid or salt or ester thereof to a salt or ester of 3-carbamoyl-3,4-epoxybutyric acid by a reaction with a base, converting the salt or ester of 3-carbamoyl-3,4-epoxybutyric acid to a salt or eter of 3-carbamoyl-3-hydroxy-4-cyanobutyric acid via reaction with cyanide, and hydrolyzing the salt or ester of 3-carbamoyl-3-hydroxy-4-cyanobutyric acid to produce citric acid or salt thereof.

B. Hydrolyzing the cyano group of 3-cyano-3-hydroxy-4-halobutyric acid or a salt or ester thereof preferably with water at a pH equal to the pH of a solution of 3-carbamoyl-3-hydroxy-4-halobutyric acid to produce 3-carbamoyl-3-hydroxy-4-halobutyric acid or an ester thereof and then performing process (A).

C. Subjecting 3-oxo-4-halobutyric acid or a salt or ester thereof to reaction with hydrogen cyanide or a salt thereof to produce 3-cyano-3-hydroxy-4-halobutyric acid or a salt or ester thereof, and then performing process (B).

D. Hydrolyzing 3-oxo-4-halobutyric acid or a salt or ester thereof, and then performing process (C).

E. Reacting 3-oxo-4-chlorobutyryl chloride with water to produce 3-oxo-4-chlorobutyric acid, reacting 3-oxo-4-chlorobutyric acid with ammonium, alkali metal or alkaline earth metal ions and with cyanide ions in an aqueous system to produce a salt of 3-oxo-4-chlorobutyric acid and HCN and reacting the salt of 3-oxo-4-chlorobutyric acid with HCN to form a salt of 3-cyano-3-hydroxy-4-chlorobutyric acid, acidifying the salt of 3-cyano-3-hydroxy-4-chlorobutyric acid with mineral acid to produce 3-cyano-3-hydroxy-4-chlorobutyric acid and an alkali metal salt of an alkaline earth metal salt, solvent extracting the 3-cyano-3-hydroxy-4-chlorobutyric acid to recover the acid from the alkali metal or alkaline earth metal salt and recovering the acid from the solvent, hydrolyzing the recovered 3-cyano-3-hydroxy-4-chlorobutyric acid to produce 3-carbamoyl-3-hydroxy-4-chlorobutyric acid, converting the 3-carbamoyl-3-hydroxy-4-chlorobutyric acid to a salt of 3-carbamoyl-3,4-epoxybutyric acid by reaction with a base, reacting the salt of 3-carbamoyl-3,4-epoxybutyric acid with mineral acid to convert the salt to an acid structure forming 3-carbamoyl-3,4-epoxybutyric acid and a salt of the mineral acid and of the base reacted in the preceding step, recovering the 3-carbamoyl-3,4-epoxybutyric acid, converting the 3-carbamoyl-3,4-epoxybutyric acid to a salt of 3-carbamoyl-3-hydroxy-4-cyanobutyric acid by reacting the acid with ammonium, alkali metal or alkaline earth metal ions and with cyanide ions in an aqueous system at a pH of from about 8 to about 14, and hydrolyzing the salt of 3-carbamoyl-3-hydroxy-4-cyanobutyric acid with a hydroxide, oxide, carbonate or bicarbonate of an alkali metal or alkaline earth metal or ammonium hydroxide or carbonate to produce a salt of citric acid.

F. Producing a compound readily hydrolyzable to citric acid or its salts by converting 3-carbamoyl-3-hydroxy-4-halobutyric acid or a salt or ester thereof to a salt or ester of 3-carbamoyl-3,4-epoxybutyric acid by a reaction with a base, and converting the salt or ester of 3-carbamoyl-3,4-epoxybutyric acid to a salt or ester of 3-carbamoyl-3-hydroxy-4-cyanobutyric acid via reaction with cyanide. This last named compound is readily hydrolyzed to citric acid by acidic hydrolysis or to citric acid salts via basic hydrolysis.

It can be seen from the foregoing that numerous new and highly useful intermediates are formed in the above process. Accordingly, this invention also provides as new compositions the following:

I. 3-cyano-3-hydroxy-4-halobutyric acid and the alkali metal, alkaline earth metal and ammonium salts thereof, particularly the compositions where the 4-halo group is 4-chloro. Salts of the alkali metals are preferred, particularly the sodium and potassium salts. The free acid itself is particularly preferred.

II. 3-carbamoyl-3-hydroxy-4-halobutyric acid and the salts thereof, particularly the compositions where the 4-halo group is 4-chloro. The free acid and the alkali metal thereof, particularly the sodium and potassium salts, are preferred.

III. 3-carbamoyl-3,4-epoxybutyric acid and the alkali metal, alkaline earth metal and ammonium salts thereof, preferably the free acid or the alkali metal salts, particularly the sodium and potassium salts.

IV. 3-carbamoyl-3-hydroxy-4-cyanobutyric acid and the alkali metal, alkaline earth metal and ammonium salts thereof particularly the salts of the alkali metals, especially the sodium and potassium salts.

V. 3-hydroxy-3,4-dicarbamoylbutyric acid and the alkali metal, alkaline earth metal and ammonium salts thereof particularly the sodium, potassium, calcium and magnesium salts.

VI. 3-carbamoyl-3-hydroxyglutaric acid and the alkali metal, alkaline earth metal and ammonium salts thereof particularly the sodium, potassium, calcium and magnesium salts.

DETAILED DESCRIPTION OF THE INVENTION

As noted above, in a preferred embodiment of the present invention a preferred starting material is a 3-oxo-4-halobutyryl halide such as 3-oxo-4-chlorobutyryl chloride. This material is readily obtained by a halogenation of diketene, a reaction that proceeds readily at temperatures from about −20°C to about 30°C. For further details reference may be had to U.S. Pat. No. 2,209,683. In general, in the process sequence involving reactions (1) through (4) above, use of chlorine compounds is preferred because of their excellent properties in subsequent processing, low cost, and ease of formation initially. It is readily appreciated that the halogen in the compounds of the early stages of the present process is primarily useful as a low cost conveniently displaceable functional group. Compounds containing other functional groups that have the desired properties are also useful in this connection such as: sulfonates, sulfates, nitrates, nitrites, phosphates and phosphites.

The 3-oxo-4-halobutyryl halide is converted into 3-oxo-4-halobutyric acid by reaction with water in a hydrolysis type reaction. Surprisingly, this reaction proceeds quantitatively and at a high rate. Preferably, it is conducted in the presence of the same solvent system that existed in the prior halogenation reaction. The acid product formed at this point is insoluble in the solvent systems described so that it readily precipitates. Hydrogen halide (HCl), the other product of the hydrolysis, evolves as a vapor phase composition. Accordingly, the solvent, as well as the product acid, is readily separated for further processing of the acid and recycle of the solvent. A typical recovery operation for the acid is filtration or centrifuging to provide the intermediate 3-oxo-4-halobutyric acid in high purity. The hydrolysis operation occurs readily in virtually 100 percent yield and conversion at a low temperature, typically from about 0 to about 50°C using a 25 percent solution of the halide in carbon tetrachloride solvent. Water is fed in about stoichiometric proportions. A typical solvent is carbon tetrachloride.

The 3-oxo-4-halobutyric acid thus obtained is then reacted in an HCN system that may contain ammonium, alkali or alkaline earth metal ions as well as cyanide ions. If the system contains approximately stoichiometric or a greater amount of ammonium, alkali or alkaline earth metal ions, the acid is converted to a corresponding ammonium, alkali or alkaline earth metal salt while the 3-oxo group is converted to a cyanohydrin. This reaction is typically accomplished by feeding hydrogen cyanide and alkali metal cyanide or alkaline earth metal cyanide. Alternately, the cyanide compound may be fed without feeding HCN and likewise hydrogen cyanide may be fed together with merely a source of the metal ions such as an alkali or alkaline earth metal hydroxide, oxide carbonate or bicarbonate or HCN can be fed to either 3-oxo-4-halobutyric acid or its salt or ester. The preferred proportions for the reaction where it is desired to make the salt are generally the equivalent of feeding one mol of alkali metal cyanide or one-half mol of alkaline earth metal cyanide per mol of 3-oxo-4-halobutyric acid. Frequently, it is desirable to enhance yields by using an excess of HCN in the system ranging up to about 3 mols of excess HCN per mol of 3-oxo-4-halobutyric acid. A typical feed in such cases is 1 mol of 3-oxo-4-chlorobutyric acid, one mol of sodium cyanide and ½ mol of HCN. It will be evident that this results in the feed of an extra half mol of cyanide per mol of 3-oxo-3-halobutyric acid; however, it has been discovered that this excess cyanide provides a substantial increase in the reaction rate and extent at this stage and in the next step to be described hereinafter and that the excess cyanide is readily recovered after the subsequent step for recycle. On the other hand, preferred proportions for producing the cyanohydrin acid directly range from 1 to 4 mols of HCN per mol of 3-oxo-4-halobutyric acid.

Typically in an alkali metal cyanide system the 3-oxo-4-halobutyric acid fed is reacted to a salt and an HCN addition occurs concurrently in the same environment wherein a 25 wt. percent solution of 3-oxo-4-chlorobutyric acid in water is combined with enough concentrated NaCN solution to produce a pH of from about 5 to about 7. This produces sodium 3-cyano-3-hydroxy-4-chlorobutyrate. Similarly, potassium-3-cyano-3-hydroxy-4-chlorobutyrate, calcium bis-3-cyano-3-hydroxy-4-chlorobutyrate, and corresponding compounds of the other alkali and alkaline earth metals or of ammonia are formed by feeding the cyanide salt of the corresponding metal or of ammonia.

The butyrate salt from the preceding step is then reacted with acid to convert the salt to a butyric acid compound. Usually this is accomplished by adding a mineral acid to the solution from the preceding step, dropping the pH to about 2.0. Typically, concentrated HCl is used. This step is omitted where the preceding step was performed with HCN as the main source of cyanide avoiding the formation of a salt requiring acidification.

The overall yield for the preceding two reactions beginning with the 3-oxo-4-halobutyric acid to produce the 3-cyano-3-hydroxy-4-halobutyric acid is about 85 percent when the excess HCN is not used in the first reaction. This yield rises to about 99 percent when using a system ratio equivalent to a feed of approximately 0.5 mols of HCN per mol of alkali metal cyanide and per mol of 3-oxo-4-halobutyric acid. Under these conditions, the conversion of 3-oxo-4-halobutyric acid to the 3-cyano-3-hydroxy-4-halobutyric acid is virtually quantitative as is the reaction of the 3-oxo-4-halobutyryl halide to produce 3-oxo-4-halobutyric acid. It is thus seen that the foregoing reactions of the present process starting with diketene to produce 3-cyano-3-hydroxy-4-halobutyric acid can be caused to occur readily in high yield generally better than 95 percent overall.

One of the advantages of having the 3-cyano-3-hydroxy-4-halobutyric acid at this point of the process is that a solvent extraction using ether as a typical solvent is possible to remove by-product salt produced when alkali metal cyanide, alkaline earth metal, cyanide or ammonium cyanide is fed as the source of cyanide in the formation of the 3-cyano-3-hydroxy-4-halobutyrate to provide a purified butyric acid compound. The acid can be recovered from the extract by evaporation of the solvent. The extract or the acid may be hydrolyzed directly by merely adding water, producing 3-carbamoyl-3-hydroxy-4-halobutyric acid. The reaction is suitably performed at a temperature of from about 0 to about 100°C. A temperature of about 40° to about 60°C is preferred for this hydrolysis, the hydrolysis being substantially faster than at about 35°C.

The system is allowed to achieve its inherent pH for the acid which is from about ½ to about 4 (measured at ~35°C) depending upon the concentration which usually ranges from about 2 to about 30 wt. percent solution of acid in water. A preferred pH range for a solution of about 10–20 wt. percent concentration is 1.5 to 2.5. Where a salt is fed, the pH is preferably adjusted by adding mineral acid to provide the pH corresponding to the acid solution of comparable concentration. In general, it is desired to avoid a pH which is more acidic than about 2.0 because then the carbamoyl groups hydrolyze to carboxyl groups.

After hydrolysis of the 3-cyano group to a 3-carbamoyl group, the 3-carbamoyl-3-hydroxy-4-halobutyric acid solution is typically heated at 30°–40°C under vacuum to remove water and residual solvent. The intermediate acid obtained at this point is of comparatively high purity. Apparently, any unreacted 3-oxo-4-halobutyric acid decarboxylates during the hydrolysis of the 3-cyano-3-hydroxy-4-halobutyric acid and is removed as a volatile by-product in the vacuum distillation.

In one type of alternate processing, the solvent extraction and recovery operations for the 3-cyano-3-hydroxy-4-chlorobutyric acid are omitted, the 3-carbamoyl-3-hydroxy-4-halobutyric acid solution resulting after hydrolysis being used directly in the subsequent reaction step described hereinafter leaving the removal of any inorganic salt present at that point for a subsequent part of the process.

The 3-carbamoyl-3-hydroxy-4-halobutyric acid resulting from the preceding hydrolysis reaction with or without co-present salt is converted to 3-carbamoyl-3,4-epoxybutyric acid or its salt by a reaction with a suitable base as defined herein. An aqueous solution of the 3-carbamoyl-3-hydroxy-4-halobutyric acid (1 mol) (2–30 wt. percent concentration), typically 10 percent, is combined per 2 equivalent mols of base (typically supplied as a 5 molal aqueous NaOH solution). The reaction proceeds rapidly, usually being complete in 30 minutes or less at room temperature. The reaction is suitably performed at temperatures from about 0° to about 100°C, producing the salt.

The intermediate 3-carbamoyl-3,4-epoxybutyric acid may be recovered in comparatively pure form by acidification of the corresponding salt with mineral acid, by cooling, and or solvent extraction if desired.

Summarizing a typical epoxidation and subsequent epoxide cleavage procedure, 3-carbamoyl-3-hydroxy-4-halobutyric acid is reacted with two equivalents of base (typically NaOH) per mol of acid at about room temperature in aqueous solution forming sodium 3-carbamoyl-3,4-epoxybutyrate. This salt is then reacted with a strong acid (typically HCl) to produce 3-carbamoyl-3,4-epoxybutyrate acid which is only moderately soluble in cold water. Thus, a crystallization process can be performed at this point if desired to remove by-product salt (NaCl) present in the system.

Following the reaction with base and the purification described if the latter is used, 3-carbamoyl-3,4-epoxybutyric acid salt derived from the resulting salt-free acid is reacted with cyanide ions to open the epoxide ring forming an alkali metal or alkaline earth metal salt of 3-carbamoyl-3-hydroxy-4-cyanobutyric acid. Preferably, if 3-carbamoyl-3,4-epoxybutyric acid is used, it is pre-reacted with base to form a salt prior to the reaction with cyanide ions. The cleavage of the epoxide also may be accomplished by feeding sodium cyanide and hydrogen cyanide together with pH control or buffer components to maintain a desired pH. This reaction liberates up to 1 mol of NaOH per mol of sodium 3-carbamoyl-3-hydroxy-4-cyanobutyrate formed.

A preferred pH range for the reaction is from about 9 to about 13.5. A particularly preferred range is from about 11.0 to about 13.2. A preferred sequence is to add 1 mol of alkali metal cyanide (NaCN) or the equivalent quantities of alkali or alkaline earth metal hydroxide or carbonate and hydrogen cyanide or other cyanide sources per mole of 3-carbamoyl-3,4-epoxybutyrate. As this system reacts, base (NaOH) (1 mol) is liberated which produces a gradually increasing pH unless pH control is used. A pH of 14 may be exceeded unless acid is added or other pH control is used to neutralize the system to maintain the desired pH. Typically, pH is measured with a glass electrode pH meter and the reaction is conducted for from about 1 to about 24 hours at a temperature of from about 10 to about 100°C.

In an alternate procedure which may be preferred in some instances where salt removal is not required at this point, the 3-carbamoyl-3-hydroxy-4-halobutyric acid is reacted with base usually producing at least in part 3-carbamoyl-3-hydroxy-4-halo butyric acid salt. This system is reacted with cyanide ions and alkali metal or alkaline earth metal ions without going through the intervening acid stage of 3-carbamoyl-3,4-epoxybutyric acid and attendant separations and even without isolation of 3-carbamoyl-3,4-epoxybutyric acid salt. Such a sequence permits economies in the amount of base required and consequently in the amount of overall mineral acid required for ultimate conversion to a citric acid product. In a typical example of this alternate procedure, the 3-carbamoyl-3-hydroxy-4-halobutyric acid is fed in a 2–30 percent, typically 10 percent, mixture in water which is combined with a base (typically a 5 molal NaOH solution) in about a 1:2 molar ratio. After an initial reaction of approximately ½ hour, approximately 1 mol equivalent of cyanide and metal or ammonium ions (typically a 5 molal solution of NaCN) is added per mol of acid initially used. The resulting mixture is then agitated for from about 3 to about 4 hours at from about 35° to about 40°C to effect substantially complete conversion to from about sodium 3-carbamoyl-3-hydroxy-4-cyanobutyrate.

It will be appreciated that the foregoing reactions with base and with the cyanide ions and with the ammonium, alkali metal or alkaline earth metal ions are suitably conducted in either batch or continuous processes in one or more steps or stages under similar or different conditions.

The foregoing reactions are also suitably performed in a continuous flow arrangement wherein the selected reactants such as base, sodium cyanide and acid are added continually.

The 3-carbamoyl-3-hydroxy-4-cyanobutyrate salt produced by the foregoing reactions is then hydrolyzed in an aqueous system preferably with acid or base present. Acid hydrolysis is usually preferred if it is desired to produce citric acid directly whereas basic hydrolysis is usually preferred to produce salts of citric acid when it is desired to avoid going through citric acid as an intermediate. Hydrolysis can be complete in one stage or operation to produce citric acid or salts of citric acid; however, it may be carried on in a plural step or plural stage operation with the production and separation or recovery of various intermediates.

In some instances it is desirable to feed initially less than a stoichiometric amount of acid or base hydrolysis reactant to bring about a partial conversion, leaving complete conversion to a subsequent step where additional reaction is fed. This is particularly helpful with basic hydrolysis to minimize by-product formation.

In some instances, partial conversion products drop out of solution as insoluble mono- or di-carboxylate precipitates, particularly when alkaline earth metal salts are formed in basic hydrolysis.

In some instances, basic hydrolysis appears to proceed through cyclic imide structures which subsequently cleave to a dicarbamoyl hydroxy carboxylic acid salt and thence to citric acid.

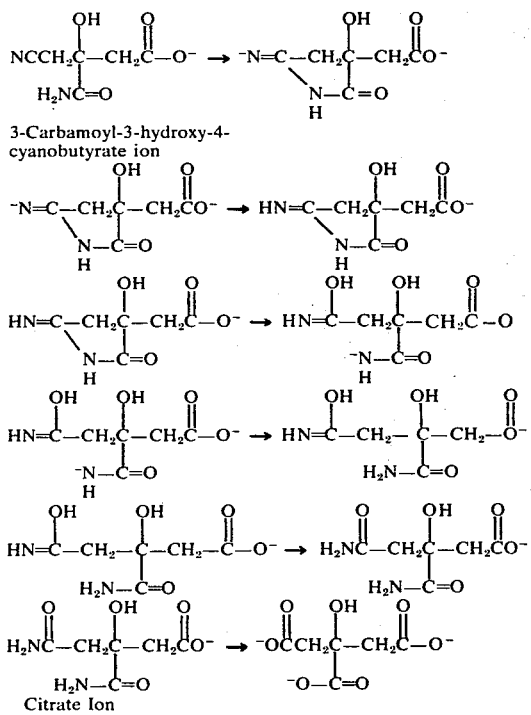

In general, the citric acid yield of the reaction in an acid hydrolysis when using excess acid at temperatures of from about 50°–250°C, preferably from about 75 to about 150, typically about 110°C at reflux of HCl (constant boiling) is virtually stoichiometric, typically 98 percent or higher. Such a high yield makes acid hydrolysis preferably in many instances even where citric acid salts are desired final products. On the other hand, acidic hydrolysis suffers from the disadvantage of production of more inorganic salts and hence is less preferred where this is an important factor. Acidic hydrolysis is followed by a neutralization with a base when it is desired to produce citric acid salts to enhance purification operations or as a final product. As with most of the other reaction steps described in the foregoing, several different intermediate stages are experienced in an acidic hydrolysis so that in effect several different reactions take place in sequence. Thus, one may deliberately seek to perform an acidic hydrolysis in two or more stages or steps; for example, an acidic hydrolysis at a pH of from about 1.5 to 3.0 to form a hydroxy dicarbamoyl acid or other acidic intermediate followed by a caustic hydrolysis at pH of 8–14, preferably 13.5–14, to convert the hydroxy dicarbamoyl acid or other intermediate to a citric acid salt.

It is evident that the three sequential reactions of epoxide formation, epoxide cleavage and basic hydrolysis can occur coincidentally at least to some extent. In general, different conditions, particularly with regard to pH, are preferred for the different reactions where maximum yields, minimum by-products and maximum rates are desired. On the other hand, it is possible, for example, to react 3-carbamoyl-3-hydroxy-4-chlorobutyric acid, base (NaOH) and cyanide (NaCN) in about a 1:2:1 molar ratio in a single system at a temperature of from about 25° to about 35°C and at a pH of from about 8 to about 14 for from about 3 to about 72 hours to produce a hydrolysis intermediate, then adding another mol of base and hydrolyzing the intermediate to trisodium citrate at temperatures of from about 35° to about 100°C. Although such a procedure is preferred where simplicity is important, the generally poorer yields usually make this procedure less desirable than in the embodiments that provide more complete separation of the three steps.

It will be appreciated that numerous additional variations of the present invention are possible now that the overall chemistry and requirements for the various intermediates necessary to produce citric acid and its salts has been discovered. Some of these variations, permutations and combinations are exemplified in the following discussion.

AMPLIFIED DESCRIPTION WITH REFERENCE TO THE FIGURES

With reference now to FIG. 1 of the drawing, the process indicated in block form therein is a preferred embodiment of the present invention providing a process for producing citric acid or its salts from a comparatively low cost and readily available starting material, diketene. It will be appreciated by those skilled in the art that diketene is readily obtained by pyrolysis of acetic acid or acetone to produce ketene and that ketene is readily dimerized to produce diketene. In the process of FIG. 1 the diketene is reacted at 10 with a halogen, typically chlorine to produce 3-oxo-4-halobutyryl halide, typically 3-oxo-4-chlorobutyryl chloride (B[C]).

The 3-oxo-4-halobutyryl chloride obtained from halogenation 10 is reacted with water at 11 in a hydrolysis reaction to produce 3-oxo-4-halobutyric acid, typically 3-oxo-4-chlorobutyric acid (C[C](H) ).

At 12, the 3-oxo-4-chlorobutyric acid is reacted with ammonium, alkali metal or alkaline earth metal ions and with cyanide ions in an aqueous system to produce a salt of 3-oxo-4-chlorobutyric acid (C[C](M) ) and HCN. The salt of 3-oxo-4-chlorobutyric acid and the HCN in turn react further to form a salt of 3-cyano-3-hydroxy-4-chlorobutyric acid (D[C](M) ).

The salt of 3-cyano-3-hydroxy-4-chlorobutyric acid is acidified with a mineral acid at 13 to produce 3-cyano-3-hydroxy-4-chlorobutyric acid (D[C](H) ) and a salt of the mineral acid and the cations reacted at 12 with the 3-oxo-4-chlorobutyric acid.

To enhance the purity of the final product, it is preferred that 3-cyano-3-hydroxy-4-chlorobutyric acid be separated from the salt produced at 13 providing a salt-free water hydrolysis at 15. The separation of salt is readily performed when desired by a solvent extraction process 14, a typical solvent being ether. The ether solvent dissolves the 3-cyano-3-hydroxy-4-chlorobutyric acid following which the acid is recovered from the solvent by vaporizing the ether solvent. Temperatures at steps 11–14 are from about 0°C to about 50°C, preferably from about 25° to about 35°C. To minimize hydrolysis of cyano groups to carbamoyl groups prior to hydrolysis at 15, it is usually preferred that the temperatures of 11–14 be below about 30°C.

In an alternate procedure, the 3-oxo-4-chlorobutyric acid from 11 is reacted at 12 directly with HCN in the absence of ammonium or metal cations to produce 3-cyano-3-hyroxy-4-chlorobutryic acid for feed to hyrolysis step 15.

The cyano group of 3-cyano-3-hydroxy-4-chlorobutyric acid recovered at 14 or of the acid from a direct HCN reaction at 12 is then hydrolyzed at 15 to a carbamoyl group to produce 3-carbamoyl-3-hydroxy-4-chlorobutyric acid (E[C]H)). Water is a suitable hydrolyzing reactant.

The 3-carbamoyl-3-hydroxy-4-chlorobutyric acid produced at 15 is then covered to a salt of 3-carbamoyl-3,4-epoxybutyric acid (F(M)) by reaction with a base in a ring formation reaction at 16.

The ring structure salt compound formed at 16 in the reaction with the base is converted at least partially to 3-carbamoyl-3,4-epoxybutyric acid (F(H)) by reaction with a mineral acid at 17. Preferably, the mineral acid used is a strong inorganic acid, typically hydrochloric acid. Strong organic acids, typically acetic acid, or oxalic acid are also suitable but generally less desirable because of greater expense per mol. This conversion to acid is desirable for one or more of several reasons. One reason is that this provides a way to remove at 18 by-product inorganic salt produced at 16 since the 3-carbamoyl-3,4-epoxybutyric acid is moderately soluble in water at low temperatures of the order of 20°C. Thus, the 3-carbamoyl-3,4-epoxybutyric acid may be recovered by a crystallization technique to provide an intermediate butyric acid compound having a reduced salt content.

If this purification is not desired, a partial acidification may still be used at 17 to provide a mixed acid-salt system feed for the next step 19 to facilitate pH control in step 19.

The 3-carbamoyl-3,4-epoxybutryic acid or acid-salt mixture obtained from 18 is converted at 19 in a complex series of interrelated reactions previously described in detail to produce a salt of 3-carbamoyl-3-hydroxy-4-cyanobutyric acid (G(M)). The amount of acid needed to be fed at this point is minimized by controlling the acid/salt ratio in the mixed product from 17, particularly in a continuous system; however, some acid addition is usually desired at 19 in batch systems to counteract the tendency toward increasing pH's brought about by the release of base (NaOH) in the course of the reaction.

The salt of 3-carbamoyl-3-hydroxy-4-cyanobutyric acid (G(M)) obtained from 19 is then hydrolyzed at 20 with a strong base to produce a citric acid salt (K(M)). Such hydrolysis produces a salt of citric acid directly. In one of numerous alternate hydrolysis procedures, the salt of 3-carbamoyl-3-hydroxy-4-cyanobutyric acid is hydrolyzed at 20 with strong acid, preferably a mineral acid such as hydrochloric acid, to produce citric acid (K(H)), Where the salt of citric acid is a more desired product of a desired acidic hydrolysis than is citric acid itself, the citric acid is readily neutralized with a base to produce the desired citric acid salt of the base. A typical base used for such a hydrolysis at this point is sodium hydroxide to produce trisodium citrate. Similarly, tripotassium citrate is produced by using potassium hyroxide and mixed sodium potassium salts can be produced by using mixed sodium and potassium oxides or hydroxides.

The recovery of product citric acid or citric acid salts from the hydrolysis effluent is suitably accomplished by any of several separation and purification operations. The purification of citric acid by calcium salt precipitation is of course well known in connection with processing of natural source citric acid and it may be used here, if desired; however, it is usually adequate and less expensive to use other procedures such as a selective crystallization of trisodium citrate in a cyclic process involving the precipitation of by-product sodium chloride or other such organic or inorganic salts.

FIG. 2 of the drawing shows broadly several key steps of the present process. The blocks indicated by reference characters 16, 19 and 20 indicate two reacting or converting stages plus a step of hydrolyzing and correspond generally to similarly numbered steps in FIG. 1.

The feed to converting step 16 is one or more of several particularly useful intermediates (E) for the preparation of citric acid; viz, 3-carbamoyl-3-hydroxy-4-halobutyric acid (E(H)) or a salt (E(M)) or ester (E(R)) thereof. The feed is reacted at 16 with a base to produce a salt (F(M)) or ester (F(R)) of 3-carbamoyl-3,4-epoxybutyric acid.

In general, the first action of the base fed at 16 is to convert any 3-carbamoyl-3-hydroxy-4-halobutyric acid E(H) present into a salt of the acid E(M), typically a sodium salt where sodium hydroxide is used as the base fed to step 16. Thereafter, the process step at 16 is a reaction of a salt or ester of 3-carbamoyl-3-hydroxy-4-halobutyric acid to eliminate halogen and form an epoxide. If desired, step 16 may be preceded by a separate step wherein 3-carbamoyl-3-hydroxy-4-halobutyric acid is converted to a salt or ester or this may be a portion of step 16 itself.

The salt or ester of 3-carbamoyl-3-hydroxy-4-halobutyric acid then reacts with base, typically the sodium hydroxide mentioned or other suitable base disclosed herein to eliminate the "4-halogen" and the hydrogen of the "3-hydroxy" group to (1) liberate water, (2) form a 3,4-expoxy compound and (3) form a salt of the halogen present in the 3-carbamoyl-3-hydroxy-4-halobutyric acid and of the cation of the base used in the reaction. Typically, the salt formed at (3) is NaCl.

The reaction at 16 is not particularly critical or sensitive with respect to pH as long as the conditions are sufficiently basic for the reactions to occur but not so basic as to produce undesired reactions such as destroying the ester if retention of the ester form is desired. Thus, in general, batchwise addition of the base used is permissible unless a progressive addition of the base is desired to maintain as high a pH as possible and at the same time minimize conversion of the ester. Of course, it is understood that the quantity of base and the conditions involved can be selected so as to deliberately convert an ester feed into a salt at this step if such is desired. A preferred feed to 16 is the acid or the salt, particularly the former because such is more readily obtained by preferred prior processing. The reaction using this feed material is conducted at a temperature from about 5° to about 100°C in from about 1 minute to about 3 hours' time.

The second step of the process of FIG. 2 is the converting step 19 wherein the salt or ester of 3-carbamoyl-3,4-epoxybutyric acid obtained from the preceding step 16 is converted to a salt or ester of 3-carbamoyl-3-hydroxy-4-cyanobutyric acid via reaction with cyanide. This step is preferably conducted in an aqueous system having a basic pH but not so basic as to convert the ester form to the salt form unless such conversion is specifically desired at this step.

The salt or ester produced at 19 is then hydrolyzed at 20 to produce citric acid or a salt of citric acid such as trisodium citrate. Typically, the citric acid or salt product is produced in hydrated form, usually the dihydrate, with the pentahydrate usually less preferred.

The hydrolysis reactions at 20 usually occur in two or more steps or stages producing numerous intermediates. It is evident that converting a salt or ester of 3-carbamoyl-3-hydroxy-4-cyanobutyric acid to citric acid requires the conversion of at least two functional groups, viz. a cyano group and a carbamoyl group. Where the feed to the hydrolysis is in the ester form, the hydrolysis in addition involves the conversion of the ester structure into an acid or salt structure liberating the alcohol constituency of the ester fed. Usually, the liberation of this alcohol provides a further complication in the somewhat involved recovery of the product citric acid or citric acid salt because of the necessity to recover the alcohol for economic or purification of product reasons. Avoidance of such problems makes the use of esters at this point generally less desired than the use of salts except where esters minimize adverse side reactions.

Typical acids preferred for hydrolysis 20, as well as at 19, 17, and 13 in FIGS. 1 and 2 are hydrochloric acid, hydrobromic acid, sulfuric acid, phosphoric acid and nitric acid. These are strong acids having an ionization constant K of $1 \times 10^{-4}$ or stronger. Of these acids, the halogen acids are frequently preferred because a preferred process for producing the starting compound, namely, 3-carbamoyl-3-hydroxy-4-halobutyric acid, involves the use of halogen so that process convenience and economies suggest a system balance around the halogen or freedom from other foreign substances. Thus, a particularly preferred mineral acid for use in hydrolysis is hydrochloric acid. Other strong acids, including organic acids such as acetic acid and oxalic acid, with ionization constants K greater than about $1 \times 10^{-5}$ are also usable at 20, 19, 17 and 13.

An acid hydrolysis 20 proceeds rapidly and to a high degree of completion in a single environment at a temperature of from about 75°C to about 150°C in from about 1 to about 48 hours.

A base hydrolysis proceeds to a high degree of completion in a single environment at a temperature from about 15°C to about 150°C in from about 1 to about 72 hours. To enhance equilibria, it is occasionally desired that even where hydrolysis 20 is suitably conducted in a single environment, that it be conducted in a staged manner under different conditions in the different stages. Such staging typically facilitates the removal of by-products such as ammonia produced in the hydrolysis. Although the hydrolysis is suitably conducted in a batchwise manner in one or more stages, it may also be conducted in a continuous manner in one or more stages in which case a staging arrangement is conveniently provided by using a tower type of countercurrent or co-current flow contacting device, typically a falling-film type of reactor or a packed tower or a perforated plate type of tower such as those used in distillation or absorption operations. A preferred contacting arrangement is a packed tower or a perforated plate tower operative at atmospheric pressure, subatmospheric pressure or superatmospheric pressure equipped with provision for a stripping operation such as with steam supplied from an external source or locally generated by means of a reboiler arrangement at the bottom of the tower with feed of the 3-carbamoyl-3-hydroxy-4-cyanobutyric acid salt or ester at the top of the tower. Such a flow arrangement provides for efficient product removal or recovery stripping of ammonia liberated in baasic hydrolysis. Other useful stripping gases are those reasonably inert or not adversely reactive in the environment, including air, nitrogen, carbon dioxide, as well as hydrocarbons such as methane, ethane, propane, butane, hydrogen and the like.

An alternate hydrolysis of the 3-carbamoyl-3-hydroxy-4-cyanobutyric acid salt or ester at 20 of FIG. 2 is a basic hydrolysis using appropriate organic or inorganic bases with the inorganic bases generally preferred. In addition to the basic hydrolysis procedures previously described, another arrangement for basic hydrolysis is what is termed a water hydrolysis accomplished by feeding essentially water utilizing the by-product ammonia liberated in the course of the reaction as a source of cations for converting the citric acid to ammonium salts. In general, such a water hydrolysis and hydrolysis using by-product or deliberately fed ammonia or ammonium compounds such as hydroxides and carbonates is so slow as to be in the less preferred category since even where ammonium salts of citric acid are the desired product, it is usually preferred to first proceed through an acid hydrolysis as described in the foregoing and follow it with a neutralization with ammonia or an ammonium compound.

In other alternate hydrolysis procedures, the fundamental hydrolysis is conducted in two steps in an acidic or basic hydrolysis to hydrolyze first one of the cyano and the carbamoyl groups following which the resultant product from the first hydrolysis is subjected to a second hydrolysis conversion of the second one of said groups. It is generally particularly preferred that where such a two-step hydrolysis is employed, the first group to be hydrolyzed is the cyano group rather than the carbamoyl group because the presence of the carbamoyl group appears to be highly desirable to bring about a rapid and complete hydrolysis of the cyano group, particularly in basic hydrolysis.

To assist basic hydrolysis and minimize the amounts of base required, the base liberated at the epoxide ring scission operation 19 can be utilized in the subsequent hydrolysis without separation or neutralization by acid for pH control at 19. Thus, the operations at 19 can be combined with at least an initial portion of the hydrolysis 20.

To do this it is desirable to avoid the operation use of acid in pH control at the epoxide cleavage operation 19. This provides an incidental benefit in a reduction of the amount of salt that must be separated from the final product.

By feeding to 19 the salt of 3-carbamoyl-3,4-epoxybutyric acid in approximately a 1 molar solution or less concentrated, the maximum achievable caustic concentration in the system will aslo be approximately 1 molar, corresponding to a pH of about 14. Thus the pH may be limited by controlling the concentration of cyanide and 3-carbamoyl-3,4-epoxybutyric acid salt without requiring feed of acid for pH control.

Letters used in the FIGS. identify the ions involved in the various systems. For example, B is 3-oxo-4-halobutyrylhalide, C is the 3-oxo-4-halobutyrate ion, C[C] is the 3-oxo-4-chlorobutyrate ion, D[C]R is an R ester of 3-cyano-3-hydroxy-4-chlorobutyric acid, E[C](H) is 3-carbamoyl-3-hydroxy-4-chlorobutyric acid, F(M) is a 3-carbamoyl-3,4-epoxybutyrate salt, G(M) is a 3-carbamoyl-3-hydroxy-4-cyanobutyrate salt, K is citrate radical, K(H) is citric acid, and K(M) is a citrate salt.

Figure 3:
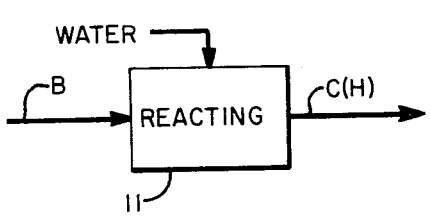
FIG. 3 illustrates a process for producing 3-oxo-4-halobutyric acid by a water hydrolysis of 3-oxo-4-halobutyryl halide.

FIG. 3 indicates in a general way the process 11 of FIG. 1 where 3-oxo-4-halobutyryl halide is hydrolyzed to produce 3-oxo-4-halobutyric acid or a salt or ester thereof. Preferably, the hydrolysis is a reaction with water. In a preferred embodiment this step receives 3-oxo-4-chlorobutyryl chloride and produces 3-oxo-4-chlorobutyric acid by a hydrolysis reaction with water. Although chlorine feed compounds are preferred, other suitable halogen compounds may be used provided the feed compound reacts with water to produce a corresponding oxo-halobutyic acid or alternately with an alcohol to produce an ester. Thus, other feed compounds for the hydrolyzing step 11 include 3-oxo-4-bromobutyryl bromide, 3-oxo-4-iodobutyryl iodide, and 3-oxo-4-fluobutyryl fluoride.

Using the other halogen compounds as feed to reactant step 11 instead of the chloro compounds exemplified produces corresponding butyrates, typically 3-oxo-4-bromobutyric acid, 3-oxo-4-iodobutyric acid and 3-oxo-4-fluobutyric acid.

It will be recognized that, although water is a preferred hydrolysis reactant for producing 3-oxo-4-halobutyrate radicals, because of the convenient reactivity and low cost, other hydrolysis reactants including acids or bases may be suitable and desirable. For example, the hydrolysis 11 may be conducted with an aqueous solution containing basic reacting cations such as ammonium, alkali metal or alkaline earth metal cations. This produces corresponding salts of 3-oxo-4-halobutyric acid directly such as sodium 3-oxo-4-chlorobutyrate.

Other typical compounds produced by a hydrolysis 11 include ammonium-3-oxo-4-chlorobutyrate, potassium-3-oxo-4-chlorobutyrate, lithium-3-oxo-4-chlorobutyrate, magnesium-bis-3-oxo-4-chlorobutyrate, calcium-bis-3-oxo-4-chlorobutyrate, strontium-bis-3-oxo-4-chlorobutyrate, barium-bis-3-oxo-4-chlorobutyrate as well as similar salts of the other alkali metals and alkaline earth metals as well as similar salts containing the other halogens in place of chlorine.

A wide variety of esters can be produced from acids produced at 11 including esters of various primary, secondary and tertiary, straight chain, branched chain, monocyclic, polycyclic, saturated, unsaturated, aromatic monobasic, dibasic and polybasic alcoholic compounds. Preferred esters include primarily the esters of alcohols having from 1 to about 20 carbon atoms per molecule, more preferably esters of the lower alkanols having up to about six carbon atoms per molecule. Thus, typical esters are those of methyl, ethyl, propyl, isopropyl, butyl, isobutyl, secondary butyl, tertiary butyl and the various pentyl and hexyl alcohols. Typical diol esters include mono and diesters of ethylene glycol, propylene glycol, butanediol and the like. Thus, typical specific esters include ethyl-3-oxo-4-chlorobutyrate, methyl-3-oxo-4-bromobutyrate, methyl-3-oxochlorobutyrate, propyl-3-oxo-4-iodobutyrate, isopropyl-3-oxo-4-fluobutyrate, and the like. Although such ester compounds may not be similarly described in such detail for each of the subsequent steps in the overall process of the present invention, it is to be understood that starting esters thus produced at an early point in the process can be carried through to produce similar corresponding esters as well as salts of the various other acids as well as the acids themselves described in connection with the other steps of the overall process.

In many instances mixed acid-salt, acid-ester, salt-ester, or acid-salt-ester systems can exist in various proportions at this and at subsequent steps of the process depending on the pH of the various systems and upon the proportions in which the reactants are used. Such compositions based on the acids, salts and esters described herein provide novel compositions of matter in themselves.

Figure 4:
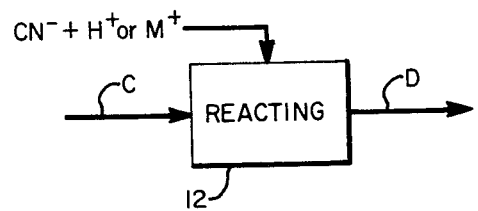
FIG. 4 shows a process for producing 3-cyano-3-hydroxy-4-halobutyric acid from 3-oxo-4-halobutyric acid by a cyanohydrination reaction in an HCN system.

With reference now to FIG. 4 of the drawing, the cyanohydrination or cyanohydration reaction step 12 of the present process is indicated. In this reacting step 12, 3-oxo-4-halobutyric acid or a salt thereof is subjected to reaction with hydrogen cyanide or a salt thereof to produce 3-cyano-3-hydroxy-4-halobutyric acid or a salt thereof.

Salts of hydrogen cyanide useful include ammonium, alkali metal and alkaline earth metal cyanides, such as ammonium cyanide, sodium cyanide, potassium cyanide, calcium cyanide, and magnesium cyanide.

In this step 3-oxo-4-halobutyric acid or a salt thereof is reacted with cyanide and hydrogen ions.

This process 12 may include an acidification (13 of FIG. 1) to produce 3-cyano-3-hydroxy-4-halobutyric acid from the corresponding salt. Thus, 3-oxo-4-halobutyric acid is reacted with a cyanide of ammonia, of an alkali metal, or of an alkaline earth metal to produce an ammonium, alkali metal or alkaline earth metal salt of 3-oxo-4-halobutyric acid and HCN. In turn, the salt of 3-oxo-4-halobutyric acid is reacted with hydrogen cyanide to produce the corresponding ammonium, alkali metal or alkaline earth metal salt of 3-cyano-3-hydroxy-4-halobutyric acid. The salt of 3-cyano-3-hydroxy-4-halobutyric acid is reacted with a strong acid to produce 3-cyano-3-hydroxy-4-halobutyric acid and an ammonium, alkali metal or alkaline earth metal salt of the strong acid.

Preferably the amount of hydrogen cyanide available to the system is an amount in excess of that released by the reaction of the 3-oxo-4-halobutyric acid with the cyanide salt.

In a preferred embodiment 3-oxo-4-halobutyric acid is reacted with HCN to produce 3-cyano-3-hydroxy-4-halobutyric acid.

A preferred feed is one or more of the keto acids described as products of the hydrolysis 11 of FIG. 3. It is to be understood, however, that the source of the 3-oxo-4-halobutyrate radicals used as feed for reacting step 12 of FIG. 4 is not limited to the process described in connection with FIG. 3 since feed 3-oxo-4-halobutyric acid obtained from any source or prior processing history is generally suitable feed for cyanohydrination as long as the purity thereof is acceptable for the reaction at 12 and the utilization of the products of that reaction.

It is to be appreciated, of course, that the process of FIG. 3 is a preferred way of producing feed acid for the cyanohydrination step 12 of FIG. 4. Thus, a particularly preferred feed for FIG. 4 is a 3-oxo-4-halobutyric acid such as 3-oxo-4-chlorobutyric acid obtained from the process of FIG. 3 when using water as a hydrolysis reactant.

Reacting step 12 of FIG. 4 forms a cyanohydrin structure at the oxo functional group of the feed 3-oxo-4-halobutyric acid or salt. Thus, a primary requirement for this reaction system is that it provide for the addition of hydrogen and cyanide to 3-oxo-4-halobutyrate radicals to produce corresponding 3-cyano-3-hydroxy-4-halobutyrate radicals. This reaction is suitably conducted in a wide variety of ways under conditions ranging from basic through neutral to acidic. If the cyanohydrination 12 of FIG. 4 is conducted in an aqueous system where the reactants fed to the step include a source of metal cations, "salt" products D(M) are formed from an "acid" feed. The preferred cations of such salt products of 12 are the alkali and alkaline earth metals. Typical preferred product compositions from reacting step 12 of FIG. 4 include sodium, potassium, magnesium, or calcium salts of 3-cyano-3-hydroxy-4-halobutyric acid, the halogen of such salts being any halogen, preferably chlorine.

Where metal cations are not available, the product from cyanohydrination 12 is usually an acid, such as 3-cyano-3-hydroxy-4-chlorobutyric acid. Such acid is obtained, for example, by reacting hydrogen cyanide with feed 3-oxo-4-chlorobutyric acid in an aqueous system containing from about 1 to about 30 wt. percent HCN and from about 1 to about 30 wt. percent 3-oxo-4-chlorobutyric acid at from about 0° to about 100°C.

In addition, 3-oxo-4-halobutyrate esters may be employed as feed to cyanohydrination 12 of FIG. 4. Such esters are preferably converted to salts at 12. Where acids are desired, they may be obtained by acidification of the salts.

Figure 5:
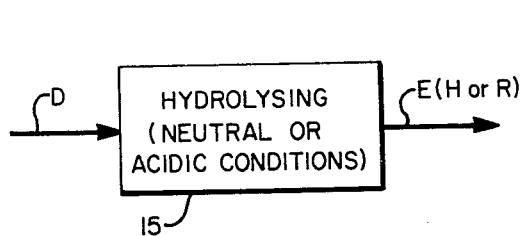
FIG. 5 shows a process for hydrolyzing 3-cyano-3-hydroxy-4-halobutyric acid to produce 3-carbamoyl-3-hydroxy-4-halobutyric acid.

With reference now to FIG. 5 of the drawing, the process step therein indicates a hydrolysis operation 15 wherein the cyano group of 3-cyano-3-hydroxy-4-halobutyric acid or a salt or ester thereof is hydrolyzed to a carbamoyl group to produce 3-carbamoyl-3-hydroxy-4-halobutyric acid or an ester thereof. This hydrolysis is suitably conducted at a pH of from about ½ to about 4 or even up to about 6.5. The hydrolysis is preferably conducted under acidic conditions no more acidic than a pH of about 2 with acid feed to avoid decompositions of the cyano group and conversion of the 3-carbamoyl group to a 3-carboxyl group. Thus, a preferred feed to hydrolysis 15 is 3-cyano-3-hydroxy-4-halobutyric acid and a preferred hydrolyzing reactant is water at a pH of from about 2 to about 4 producing 3-carbamoyl-3-hydroxy-4-halobutyric acid.

Typical acids produced in this way are 3-carbamoyl-3-hydroxy-4-chlorobutyric acid, 3-carbamoyl-3-hydroxy-4-bromobutyric acid, 3-carbamoyl-3-hydroxy-4-iodobutyric acid and 3-carbamoyl-3-hydroxy-4-fluobutyric acid. Although such processing usually is in a less preferred category, the hydrolysis of the cyano group also may be conducted when feeding corresponding esters and even corresponding salts in which case the hydrolysis usually operates under more nearly neutral conditions; however, even here it is preferred that basic conditions be avoided. Where permissible, the maintenance of acidic conditions may be enhanced when feeding esters and salts by the feed of a mineral acid as defined herein or other suitable acids of the type used as catalysts in ester formation. A typical acid is HCl.

Other typical compounds produced by hydrolysis 15 include methyl-3-carbamoyl-3-hydroxy-4-chlorobutyrate, sodium-3-carbamoyl-3-hydroxy-4-bromobutyrate, isopropyl-3-carbamoyl-3-hydroxy-4-butyrate.

Figure 6:
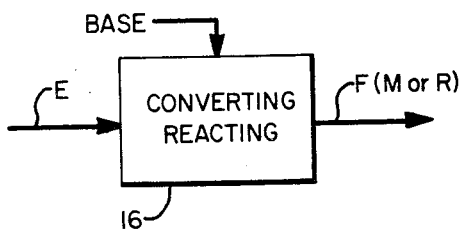
FIG. 6 shows a process for the epoxidation of 3-carbamoyl-3-hydroxy-4-halobutyric acid to form an epoxide derivative thereof.

FIG. 6 indicates a converting-reacting step 16. In this step 3-carbamoyl-3-hydroxy-4-halobutyric or a salt or ester thereof is converted to a salt or ester of 3-carbamoyl-3,4-epoxybutyric acid by a reaction with a base. In this operation any free acid present is neutralized to produce a generated salt and then said generated salt or said salt or ester is converted to a structure containing a 3,4-epoxy group by dehydrohalogenation. Although the preferred material epoxidized at 16 is a salt or ester, particularly the former such as 3-carbamoyl-3-hydroxy-4-chlorobutyric acid salt obtained by neutralization of the acid from step 15 of the process of FIG. 5, the feed to 16 for epoxidation is also suitably the acid, additional base cations being provided to 16 to provide the salt equivalent.

In any event, 3-carbamoyl-3-hydroxy-4-halobutyrate radicals are reacted at 16 with a base as herein defined to form 3-carbamoyl-3,4-epoxybutyrate radicals. Also formed at this step is by-product salt derived from reaction of the cation component of the base with the halogen of the feed 3-carbamoyl-3-hydroxy-4-halobutyrate radicals.

For the complete conversion of feed acid to 3-carbamoyl-3,4-epoxybutyrate acid salt, 2 mols of an alkali metal or ammonium base or 1 mol of an alkaline earth metal base is used per mol of feed 3-carbamoyl-3-hydroxy-4-halobutyric acid. Of course, it is evident that the foregoing amount of base required for the production of 3-carbamoyl-3,4-epoxybutyric acid, salt or ester is reduced by half where the feed to converting step 16 is already in salt or ester form unless of course it is desired that the converting step 16 also convert an ester feed into a salt product in which case the full number of equivalents of basic reacting substance is required. Although inorganic bases such as the hydroxides, oxides, carbonates and bicarbonates of the alkali or alkaline earth metals are preferred for reaction at 16, strong organic bases such as quaternary ammonium hydroxides or ion exchange resins having fixed cationic sites are also useful at 16 to produce corresponding salts of the organic base where such salts are desired as a specific product or as an intermediate for use in a subsequent step of the present citric acid process.

It will be appreciated from the foregoing discussion that upon completion of the epoxidation of converting step 16 of FIG. 6, the variety of the earlier compositions with regard to halogen content is no longer evident. Thus, in general, the 3-carbamoyl-3,4-epoxybutyrate radicals produced at 16 are substantially independent of the halogen constituency of the preceding compounds. On the other hand, it is to be observed that cost is usually a significant factor in the production of any chemical composition and that therefore a preferred halogen constituent of the preceding compounds is one that will produce the 3-carbamoyl-3,4-epoxybutyrate radicals at the lowest price. From such considerations as these, it is generally preferred that the halogen compounds which precede the 3-carbamoyl-3,4-epoxybutyric acid be chlorine compounds or, to a lesser extent, bromine compounds.

Figure 7:
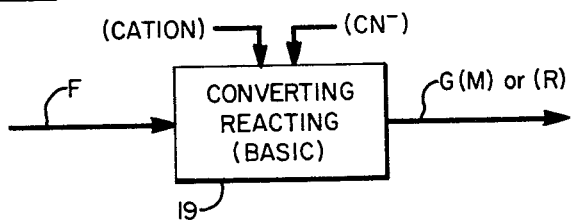
FIG. 7 shows an epoxide scission process whereby the epoxy structure of the epoxide derivative of 3-carbamoyl-3-hydroxy-4-halobutyric acid is converted to a 3-carbamoyl-3-hydroxy-4-cyanobutyric acid compound.

In Step 19 of FIG. 7 a salt or ester of 3-carbamoyl-3,4-epoxybutyric acid is converted to a salt or ester of 3-carbamoyl-3-hydroxy-4-cyanobutyric acid via reaction with cyanide. Preferably, the reaction is under basic conditions and in an aqueous system. Preferably, the system contains ammonium, alkali metal or alkaline earth metal cations in an amount of at least two ammonium or alkali metal cations or one alkaline earth metal cation per 3-carbamoyl-3,4-epoxybutyrate anion and at least one cyanide cation per 3-carbamoyl-3,4-epoxybutyrate anion. Hydroxide ions are formed in the reaction. As discussed in connection with FIGS. 1 and 2 in some instances a preferred feed for Step 19 to assist in pH control is a 3-carbamoyl-3,4-epoxybutyrate acid/salt mixture. Typically, at least a part of each of the cyanide ions and the ammonium, alkali metal or alkaline earth metal cations is provided by feeding a chemical compound containing both, typically an alkali metal cyanide, or by feeding two compounds such as HCN and alkali hydroxide or HCN and alkali metal cyanide.

Thus, typical feed to converting step 19 of FIG. 17 is a 3-carbamoyl-3,4-epoxybutyrate in acid, salt or ester form or a mixture of two or more of the acid, salt or ester while the corresponding product from the step is a 3-carbamoyl-3-hydroxy-4-cyanobutyrate salt or ester or mixture of salt and ester.

Figure 8:
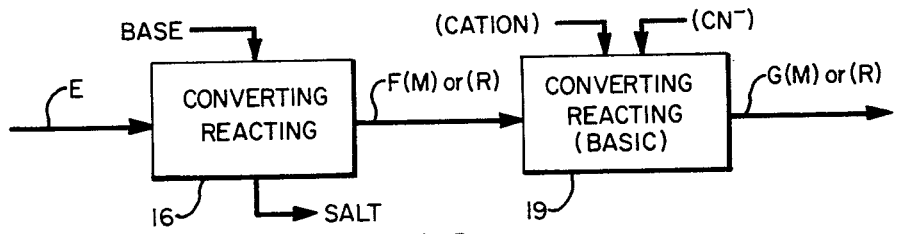
FIG. 8 shows a coordinated combination of the two steps of FIGS. 6 and 7 to indicate a particularly significant subcombination of the overall process.

FIG. 8 indicates a coordinated two-step operation where the first step is the epoxidation or converting-reacting step 16 described in connection with FIG. 6 and the second step is the epoxide cleavage of converting-reacting step 19 described in connection with FIG. 7. This figure shows the coordination in which the converting-reacting step 16 of FIG. 6 receives acid, ester or salt feed to produce the epoxide salt or ester intermediate which intermediate is fed directly to the converting-reacting step 19 for cleavage of the epoxide to form cyano and hydroxy structures to produce 3-carbamoyl-3-hydroxy-4-cyanobutyric acid, salt or ester. The system of the figure may operate with the salt form throughout, receiving a salt form at the feed to 16, providing a salt form product from 19.

Figure 9:
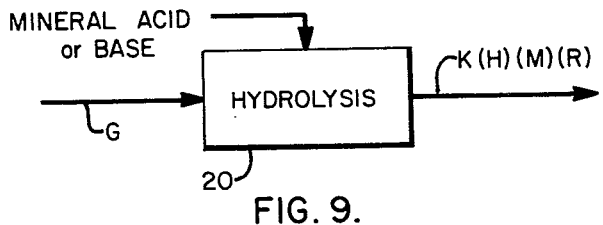
FIG. 9 indicates separately a hydrolysis process whereby a 3-carbamoyl-3-hydroxy-4-cyanobutyric acid compound is converted to a citric acid compound.
Figure 10:
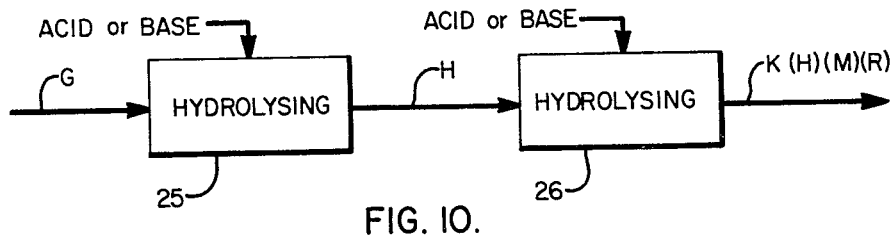
FIG. 10 illustrates the plural step hydrolysis of 3-carbamoyl-3-hydroxy-4-cyanobutyric acid compounds to produce one or more intermediate compounds in a first step and then to convert said intermediates to citric acid compounds in a subsequent step.

FIGS. 9 and 10 indicate hydrolysis details. These figures compare a "one-step" hydrolysis process (FIG. 9) in which 3-carbamoyl-3-hydroxy-4-cyanobutyric acid, salt or ester is converted directly to citric acid in an acidic hydrolysis or to a citric acid salt in a basic hydrolysis versus a "plural step" hydrolysis process (FIG. 10) in which one or more intermediates are formed. FIG. 10 illustrates feeding part of the hydrolyzing reactant or reactants (acid or base) at step 25 and feeding at step 26 another part of hydrolyzing reactant or reactants required for the hydrolysis. This illustrates numerous variations in intermediates formed in the process; such as, 3-hydroxy-3,4-dicarbamoylbutyric acid and its salts and esters, 2-carbamoylmethyl-2-hydroxy succinic acid and its salts or esters, and 3-carbamoyl-3-hydroxyglutaric acid and its salts or esters. In addition, this stepwise conversion also represents the various esters and salt-esters of citric acid that result when using ester feed to hydrolysis 25.

The various intermediate compositions involved in this last part of the process as well as elsewhere in the process have independent utility other than for use in carrying on the present process to produce citric acid. In general, all of the compositions have useful surface active properties themselves as detergents or builders, for example, and provide useful intermediates for other reactions because of the numerous functional groups contained therein. Since all of the intermediate compositions contain carboxyl groups, they are useful to form esters, as plasticizers, as intermediates for use in other reactions, and in numerous similar and related applications. Among the salt compositions produced, the salts of the alkali and alkaline earth metals are usually preferred, particularly salts of the former category such as salts of sodium or potassium.

The reactions of the present process are for the most part ionic reactions in liquid reaction media in which the systems behave as mixtures of the various ions present rather than as individual compounds. The preferred liquid reaction media or solvent for the present largely ionic process is water because it is readily available, is low in cost and has excellent solubility properties for the various reactants and intermediates involved. Other protic solvents such as alcohols and alcohol-water mixtures are also useful, particularly alkanols, typically methanol, ethanol, and methanol-water or ethanol-water mixtures. Similarly, glycols provide useful solvents, alone or in admixture with water. Typical glycol systems include ethylene glycol, propylene glycol, and ethylene glycol-water mixtures.

The use of the ester form of the intermediates expands the variety with regard to solvent or diluent systems to include systems containing other materials such as substituted and unsubstituted cyclic, acyclic and aromatic hydrocarbons including paraffins, olefins, ethers, ketones, aldehydes, esters, water immiscible alcohols, alkanols, and the like.

In the several steps of the process where solvents are used for purposes other than as reaction media, for example, in solvent extraction, preferred solvents have been mentioned as ether, particularly diethyl ether, acetone, methanol, as well as hydrocarbon such as pentane, hexane, and the like. With regard to the solvent systems useful for the halogenation of diketene, preferred solvents are low boiling solvents for the diketene which are inert to the reactants under the conditions of use such as carbon tetrachloride, ethylene dichloride, propylene dichloride, and carbon disulfide.

In a sense, with ionic systems, the distinctions between the various forms or categories of acid, ester and salt may in some instances depend on extrinsic factors such as pH of the system and on the presence of other materials. Some of the reactions disclosed require certain acidity values in order to proceed at acceptable rates whereas with some of the compounds it is important to avoid certain acidity values to avoid undesired side reactions.

Since the molecules of the present composition involve several functional groups closely associated, there are interactions that promote unexpected reactions and which inhibit some expected reactions. Thus the present compositions and compounds exhibit a high degree of unpredictability as far as the properties of the various individual functional groups are concerned as well as with regard to the properties of the compounds themselves. As a practical matter, in several instances the present invention utilizes interactions of the functional groups to assist desired reactions and suppress other reactions.

The following examples indicate preferred embodiments of the present invention.

EXAMPLE I

Preparation of 3-Oxo-4-Chlorobutyric Acid

A solution of 3-oxo-4-chlorobutyryl chloride was prepared by passing in 0.645 mols of $Cl_2$ gas into a solution of 0.645 mol of diketene at −20°C in 1,2-dichloroethane which was approximately ⅔ solvent by volume. The starting diketene was of approximately 98.1 percent purity as assayed by NMR spectroscopy. The solution was then treated in a three neck flask fitted with thermometer, dropping funnel, condenser, mechanical stirrer and a $N_2$ inlet and outlet with 11.8 ml of water (0.655 mol) added slowly from the dropping funnel. A slow stream of $N_2$ gas was passed through the flask and allowed to pass out the condenser and into a NaOH solution prepared from 80 ml of 7.93 N NaOH (0.635 mol) diluted to approximately 800 ml. The water was added with vigorous stirring at such a rate that no HCl escaped the NaOH trap while maintaining a temperature of 25°–30°C in the reaction mixture. The product acid began to crystallize from the reaction mixture about ⅓ of the way through the addition of water. After completion of the addition, stirring was continued overnight. The NaOH trap solution was then made up to 1 liter and a 100 ml aliquot removed. This was titrated to a phenolphthalein end point requiring 3.23 ml of 0.1043 N HCl showing a net excess of 3.36 milliequivalents of unused base remained. This corresponds to a 99.8 percent yield of HCl based on diketene. The solid acid was recovered by filtration and yielded 61.1 g (70.8 percent of theory) of snow white crystalline product MP 69°–71°C. Further washing of the flask with pentane removed 1.32 g of solids. 21.3 g of acid was recovered upon evaporation of the residual solvent filtrate at room temperature on a rotary evaporator under vacuum. Both solid products were washed with pentane and found to be pure via their NMR spectra. The combined yield was 83.7 or 97 percent of theory. The melting point reported by Rosdig, Kleppe and Markl is 67°–69°C (Ber. 95 1252 (1962).

Preparation of 3-cyano-3-Hydroxy-4-Chlorobutyric Acid 68.8 g of 3-oxo-4-chlorobutyric acid (94.2 percent purity by NMR) (0.476 mols) was mixed with 200 ml of distilled water in a three neck flask fitted with a thermometer, dropping funnel, stirrer and connected via an ice condenser to a nitrogen bubbler which was connected to a NaOH trap in series. Sodium cyanide (24.5 g) (0.50 mol) was dissolved in 75 ml of water and placed in the dropping funnel. The contents of the flask were cooled in an ice bath and the NaCN solution added at 10°–15°C to give a pH of 8. The mixture was brought to a pH of 0.8 with 46 ml (0.568 mol) concentrated HCl and then extracted with five 100 ml. portions of ether. The combined ether extract was dried with anhydrous $MgSO_4$. After filtering off the drying agent and washing the solids with ether, the ether was evaporated on a rotary evaporator at 35°–40°C. Assay of the 78.3 g of product by NMR showed 80.6 percent 3-cyano-3-hydroxy-4-chlorobutyric acid, 8.22 percent water, 3.53 percent acetoacetic acid and 7.6 percent ether. The last traces of ether and water were quite difficult to remove. The yield was 82 percent.

Preparation of 3-Carbamoyl-3-Hydroxy-4-Chlorobutyric Acid 68.27 g (0.5 mol) of 3-oxo-4-chlorobutyric acid was placed in 200 ml of water. To this was added a solution of 24.5 g (0.5 mol) NaCN in 75 ml of water at 10°–15°C from a dropping funnel. The resulting pH was 5.9 . Additional NaCN solid (0.3 grams) was dissolved in the reaction mixture to give a pH of 7.8. After 30 minutes, 44 ml of concentrated HCl (about ½ mol) was added to bring the pH to 1.0. The reaction mixture was then extracted with seven 100 ml portions of ether and the ether extracts combined. The ether solution was dropped into 200 ml of water at 50°C, distilling the ether off as rapidly as it could be condensed. The aqueous solution was heated for 165 minutes at 50°C after ether distillation ceased. The NMR spectrum showed that essentially all of the cyanohydrin had been converted to the corresponding carbamoyl compound. The aqueous solution was placed in a continuous ether extractor and allowed to extract overnight. During this time 19.2 g of 3-carbamoyl-3-hydroxy-4-halobutyric acid crystallized from the reboiler.

The remaining aqueous solution was stripped under high vacuum on a rotary evaporator heated to maintain a temperature of 20°–30°C. The contents of the flask became solid and after being broken up was transferred to a vacuum desiccator where drying was completed. The combined weight of solids was 64.0 g or 88.8 percent yield.

A sample was titrated to a phenolphthalein end point. 0.19475 g was required 7.70 ml of 0.1326 N NaOH corresponding to an equivalent weight of 190.7 (theory = 181.6). This is probably slightly high due to residual moisture as well as due to indicator color change at 9 to 11 whereas a titration curve indicates a neutralization end point at a pH = 7.7. Elemental analysis of a recrystallized sample gave the following results.

|   | Wt. Percent | |
|---|---|---|
|   | Theory | Found |
| C | 33.07 | 32.48 |
| H | 4.44 | 4.12 |
| N | 7.71 | 7.96 |

Preparation of 3-Carbamoyl-3,4-Epoxybutyric Acid 235.6 g of 3-carbamoyl-3-hydroxy-4-chlorobutyric acid (96.0 percent assay) (1.25 mols) which had been recrystallized from acetone was suspended in 800 ml of water and 100 g of NaOH dissolved in 100 ml of water (1.25 mols) was added while maintaining the temperature at about 15°C. After ½ hour, the pH was brought to about 2 by the addition of concentrated HCl (approximately 1.25 mols). The mixture was cooled to about 5°C whereupon solid 3-carbamoyl-3,4-epoxybutyric acid slowly crystallized. After 2 hours, 62.3 g of pure solid product was obtained in 34 percent yield. Assay of solutions showed essentially quantitative conversion of the 3-carbamoyl-3-hydroxy-3-chlorobutyric acid to 3-carbamoyl-3,4-epoxybutyric acid.

Preparation of
3-Carbamoyl-3-Hydroxy-4-Cyanobutyric Acid 43.5 g (0.3 mol) of the 3-carbamoyl-3,4-epoxybutyric acid was placed in 150 ml of water and 50.2 ml of 5.98 M NaOH solution (0.3 mol) added at 15°C. The pH of the solution was 12.07. 16.2 g of NaCN (0.33 mol) dissolved in 50 ml of water was then added at 15°C. The pH changed to 12.28. The temperature was then raised to 33°–35°C over about 10 min. 6.73 N HCl (approximately 0.3 mol) was then added slowly to maintain the pH at 11. After 27 hrs the solution was assayed by NMR analysis and showed a 101±2 percent yield of the 3-carbamoyl-3-hydroxy-4-cyanobutyric acid salt.

Preparation of Trisodium Citrate 30.0 ml of a 0.60 M (0.018 mol) solution of sodium 3-carbamoyl-3-hydroxy-4-cyanobutyrate, 0.6 M in NaCl (0.018 mol) was mixed with 3.1 ml of a 5.98 M NaOH solution 90.0186 mol) giving a pH of 13.22. After standing for 26½ hrs a 20 ml aliquot (0.0108 mol) was removed. Addition of 2.1 ml of 5.98 M NaOH (0.0108 mol) to the aliquot followed by heating the mixture 17 hrs at 100°C gave 3.89 solids containing sodium citrate and sodium chloride on evaporation and drying in a vacuum desiccator. The theoretical weight is 3.85 g. The NMR spectrum of the solution prior to evaporation showed essentially pure citrate with traces of acetate. This assay indicated 94.4 mol percent citrate and 5.6 mol percent acetate.

EXAMPLE II

A 50 percent (wt.) solution of diketene in carbon tetrachloride was prepared. Chlorine in diluent nitrogen (mol ratio 1 $Cl_2$:3 $N_2$) was bubbled in at 20°C and about 1 atmosphere pressure until chlorination was complete. The product was 3-oxo-4-chlorobutyryl chloride.

To a stirred flask at 30°C containing 3-oxo-4-chlorobutyryl chloride in carbon tetrachloride resulting from halogenation as in the previous example, a stoichiometric amount of water was added in a dropwise manner. An insoluble precipitate of 3-oxo-4-chlorobutyric acid was formed and recovered by filtration. HCl was liberated and evolved as a gas.

A 25 wt. percent aqueous solution of 3-oxo-4-chlorobutyric acid was prepared and a concentrated (6.7 molal) solution of sodium cyanide in water was added slowly to produce a system with a pH of 6–7. This produced an aqueous solution of sodium-3-cyano-3-hydroxy-4-chlorobutyrate.

To the solution of sodium-3-cyano-3-hydroxy-4-halobutyrate was added concentrated HCl to drop the pH to about 1.0 forming 3-cyano-3-hydroxy-4-chlorobutyric acid.

The 3-cyano-3-hydroxy-4-chlorobutyric acid was then extracted from the water using diethyl ether to separate the product acid from by-product NaCl.

The ether extract was then added to water at 50°C to hydrolyze the cyano group to the carbamoyl group producing 3-carbamoyl-3-hydroxy-4-chlorobutyric acid. The system was then subjected to vacuum evaporation at 30°–40°C producing a high purity product in an overall yield of 86 percent from the 3-oxo-4-chlorobutyric acid. The yield from diketene to 3-oxo-4-chlorobutyric acid was virtually quantitative.

A 10 percent by weight solution in water of 3-carbamoyl-3-hydroxy-4-chlorobutyric acid was then prepared. To this was added a 5 molal aqueous solution of NaOH in proportions of one mol of acid per two mols of NaOH. The solution was stirred for ½ hour at 35°–40°C. The product sodium-3-carbamoyl-3,4-epoxybutyrate was allowed to remain in solution. The yield as determined by NMR was virtually quantitative.

To this solution of sodium-3-carbamoyl-3,4-epoxybutyrate was added a 5 molal aqueous solution of NaCN in proportions of 3 mols per mol of sodium-3-carbamoyl-3,4-epoxybutyrate. The system was agitated for about 4 hours at 35°–40°C. The yield to sodium-3-carbamoyl-3-hydroxy-4-cyanobutyrate was virtually quantitative as determined by NMR.

The sodium-3-carbamoyl-3-hydroxy-4-cyanobutyrate was then acid hydrolyzed to citric acid by the addition of an equal volume of concentrated HCl. The system was gently heated at ~100°C for about 7 hours in an open beaker. During this heating time the volume was reduced to about one-fourth of the original volume. The solution was then evaporated to dryness under vacuum and the solids extracted with acetone. Evaporation of the acetone extract gave a syrup of citric acid which was taken up in methanol and neutralized with sodium methoxide to precipitate trisodium citrate. The product was relatively pure and white.

The foregoing reactions were analyzed at each step by NMR to determine progress and confirm a substantial absence of side reactions.

EXAMPLE III

Preparation of
Sodium-3-Carbamoyl-3,4-Epoxybutyrate 29.3 Grams of 3-cyano-3-hydroxy-4-chlorobutyric acid of 88 percent purity containing 12 percent diethyl ether from an ether extraction of product from a prior reaction was added to 50 grams of water at 25°C and then the resulting mixture was heated to 55°C for 3 hours. Following this, the heat was removed and the solution cooled to about 35°C in 30 minutes. The resulting product 3-carbamoyl-3-hydroxy-3-halobutyric acid was analyzed by NMR (Nuclear Magnetic Resonance) showing 2 AB patterns at ~3.75 (the 4-chloromethyl structure) and at ~2.85 (the methylene in the 2-position).

The 3-carbamoyl-3-hydroxy-4-halobutyric acid from the preceding step was stirred in an ice bath and kept there while a solution of 12.8 grams of sodium hydroxide in 20 ml of water was added over a 15 minute period with cooling. After 45 minutes, the product was analyzed by NMR indicating substantially complete formation of epoxide (AB pattern centered at ~2.705, J = 17 Hz).

EXAMPLE IV

Preparation of
Sodium-3-Carbamoyl-3-Hydroxy-4-Carbamoyl Butyrate

A 3.05 gram (21 millimols) sample of 3-carbamoyl-3,4-epoxybutyric acid was neutralized with 1.78 grams (21 millimols) of sodium bicarbonate in 10 ml of water.

Then 3 drops of Thymol blue (pH 8.0–9.6) were added. Then 1.09 grams (21 millimols) of sodium cyanide in 5 ml of water was added over a 10 minute period. During this period 5 molar acetic acid was added dropwise to hold the pH at about 9.1.

NMR analysis was made after 1 hour showing decreasing epoxide AB pattern along with decreasing 2 position methylene of the epoxide and with increasing 2 position methylene of 3-carbamoyl-3-hydroxy-4-cyanobutyric acid salt (~4 Hz upfield from the 2 position methylene of the starting epoxide) and with increasing cyanomethylene.

The foregoing composition was allowed to stand at room temperature for approximately 3 hours. The pH had increased to 10.5. Acetic acid was added to drop the pH to 9.1. NMR analysis was again run showing further exposide decrease and further increase of the cyanide derivative.

The sample was then allowed to stand at room temperature for approximately 15 hours and again analyzed by NMR. Virtually all epoxide spectra had disappeared, the cyano compound content had decreased and new spectra appeared indicating the presence of a different structure. The new spectra was identified as characteristic of the product obtained by conversion of the cyano group to the carbamoyl group.

EXAMPLE V

Preparation of Citric Acid

A 50 ml beaker equipped with a magnetic stirrer and a glass electrode pH meter was charged with 2.89 grams (20 millimols) of 3-carbamoyl-3,4-epoxybutyric acid and 10 ml of water. Potassium carbonate (1.38 grams, 10 millimols) was added to form potassium-3-carbamoyl-3,4-epoxybutyrate. The temperature was 35°–36°C.

To this was added 1.35 grams (20 mmols) of potassium cyanide in one portion with stirring. The pH was monitored continuously with the pH meter and controlled at 9.70 to 9.80 by adding 5 molar acetic acid dropwise.

After 15 minutes another 1.35 grams (a second mol equivalent) of potassium cyanide was added.

After a total of 130 minutes from the first addition of potassium cyanide, the system had a pH of 6.5 and by NMR analyzed only about 5 to 8 percent epoxide content. Then α-hydroxy isobutyric acid was added as an internal standard. The yield conversion of starting epoxide to potassium-3-carbamoyl-3-hydroxy-4-cyanobutyrate was calculated at this point as virtually 100 percent.

After a total of 180 minutes from the initial KCN addition, with the pH at 6.5, 8 ml of concentrated HCl (96 mmol) was added to the mixture and the resulting mixture at a pH of ≦ 1 was agitated at 55°C for 18.5 hours. An NMR analysis was then run using an internal standard showing a conversion of 87 percent of the potassium-3-carbamoyl-3-hydroxy-4-cyanobutyrate to citric acid and carbamoyl intermediate.

The mixture was stirred another 20 hours at 55°C to 80°–85°C. After 0.8 hours at this temperature, the formation of a white solid precipitate was noted. After a total of 4 hours at 80°–85°, the heating was discontinued and the mixture allowed to cool to room temperature. 13.26 grams of liquid was decanted leaving 3.77 grams of solid. The liquid was analyzed by NMR, showing citric acid with residual incompletely hydrolyzed material.

The liquid was then heated to 85°C and held at that temperature for about 16 hours to complete the conversion to citric acid.

EXAMPLE VI

A 40 ml beaker equipped with a magnetic stirrer was charged with 2.90 grams (20.0 millimols) of 3-carbamoyl-3,4-epoxybutyric acid. This material was neutralized with 20 millimols of a standard 0.898 molar NaOH solution. Then 1.29 grams of 95 percent NaCN (25 millimols) was added in one portion and the pH was maintained at 8.0 by adding 5.43 molar acetic acid dropwise from a burette. The temperature was 35°–36°C.

After 125 minutes the system pH was dropped to 7.1 by additional acetic acid, then stirred overnight at 33°C.

The NMR spectrum indicated 85–95 percent conversion of the sodium 3-carbamoyl-3,4-epoxybutyrate to sodium 3-carbamoyl-3-hydroxy-4-cyanobutyrate.

The solution was transferred to a flask equipped with a magnetic stirrer and 10 ml of concentrated HCl (120 millimols) was added. The solution was heated at 110°C for 4 hours. Additional HCl (5 ml) was added. Two hours later the solution contained only 5 percent 3-carbamoyl-3-hydroxy-4-cyanobutyric acid. At this point an additional 10 ml of HCl was added. Two hours later the solution contained only 2 percent 3-carbamoyl-3-hydroxy-4-cyanobutyric acid. Hydrolysis was continued overnight. Hydrolysis conversion of sodium 3-carbamoyl-3-hydroxy-4-cyanobutyrate to citric acid was 98 percent. Overall conversion to citric acid from starting 3-carbamoyl-3,4-epoxybutyric acid was 84 percent.

EXAMPLE VII

A 40 ml beaker equipped with a magnetic stirrer was charged with 2.90 grams (20 millimols) of 3-carbamoyl-3,4-epoxybutyric acid. The acid was neutralized to a pH of 7.0 by adding a 0.898 molar solution of NaOH. This formed sodium 3-carbamoyl-3,4-epoxybutyrate. Then sodium cyanide, 1.29 grams (25 millimols) was added in one portion. Thereafter the pH was maintained at 11.0 by the addition of 6.73 molar HCl. Temperature was 30°–31°C.

After 151 minutes an additional 1.29 grams of NaCN was added. After 205 minutes from the start, the system was analyzed by NMR showing about 5 percent 3-carbamoyl-3,4epoxybutyric acid remaining. The pH was 11.15.

The solution was then heated to 70°C over a 25 minute period and held at that temperature for about 35 minutes. The pH dropped to 9.48 indicating consumption of caustic. As heating at 70°C continued, NaOH was added periodically to maintain a pH of 10.2. After 130 minutes heating at 70°C, NaOH was added to provide a pH of about 14 and the system was heated overnight at 75°C.

The system was cooled, methanol added, and the solids filtered providing 5.4 grams of a white free flowing product.

I claim:

1. 3-hydroxy-3,4-dicarbamoylbutyric acid and the alkali metal, alkaline earth metal and ammonium salts thereof.

2. As a composition according to claim 1, 3-hydroxy-3,4-dicarbamoylbutyric acid.

3. As a composition according to claim 1, a sodium, potassium, or calcium salt of 3-hydroxy-3,4-dicarbamoylbutyric acid.

4. As a composition of matter according to claim 1, the sodium salt of 3-hydroxy-3,4-dicarbamoylbutyric acid.

5. As a composition of matter according to claim 1 the calcium salt of 3-hydroxy-3,4-dicarbamoylbutyric acid.

* * * * *

UNITED STATES PATENT OFFICE
CERTIFICATE OF CORRECTION

PATENT NO. : 3,960,941
DATED : JUNE 1, 1976
INVENTOR(S) : KARL E. WIEGAND

It is certified that error appears in the above-identified patent and that said Letters Patent are hereby corrected as shown below:

Title Page, Item [56] reads -- Migydichian --, should read -- Migrdichian --.

Column 4, Equation 5, reads --
$$NC-CH_2\underset{\underset{O=CNH_2}{|}}{\overset{\overset{OH}{|}}{C}}-CH_2\overset{\overset{O}{\|}}{C}-OM$$
--, should read --
$$NC-CH_2-\underset{\underset{O=CNH_2}{|}}{\overset{\overset{OH}{|}}{C}}-CH_2\overset{\overset{O}{\|}}{C}-OM$$
--.

Column 4, Equation 6(b), reads -- O 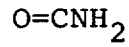 --, should read --  --.

Column 5, line 51, reads -- eter --, should read -- ester --; line 67, after "Hydrolyzing", insert -- 3-oxo-4-halobutyryl halide to produce --. Column 10, line 67, reads -- to from about so- --, should read -- to so- --.

UNITED STATES PATENT OFFICE
CERTIFICATE OF CORRECTION

PATENT NO. : 3,960,941
DATED : JUNE 1, 1976
INVENTOR(S) : KARL E. WIEGAND

It is certified that error appears in the above—identified patent and that said Letters Patent are hereby corrected as shown below:

Column 11, line 39, the equations should read as follows:

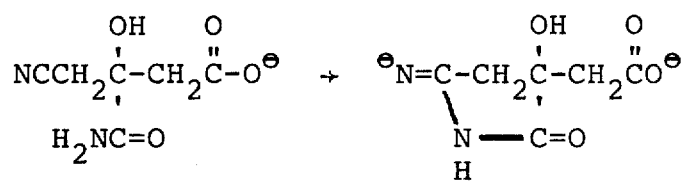

3-Carbamoyl-3-hydroxy-4-cyanobutyrate ion

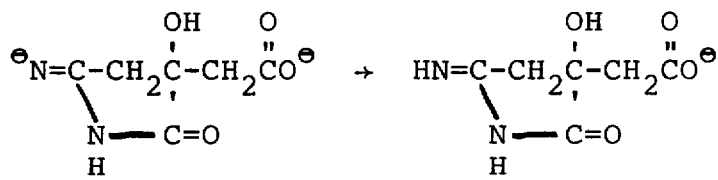

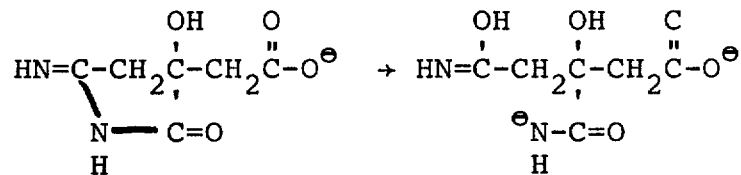

UNITED STATES PATENT OFFICE
CERTIFICATE OF CORRECTION

PATENT NO. : 3,960,941
DATED : JUNE 1, 1976
INVENTOR(S) : KARL E. WIEGAND

It is certified that error appears in the above-identified patent and that said Letters Patent are hereby corrected as shown below:

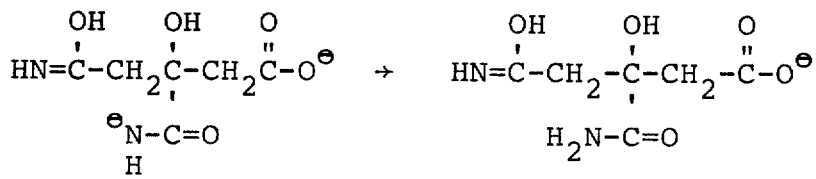

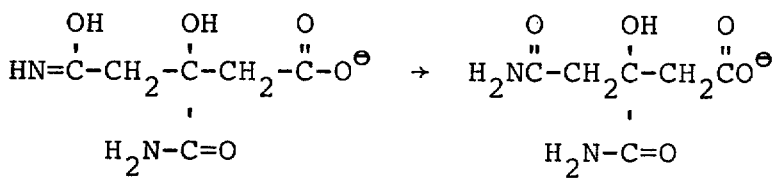

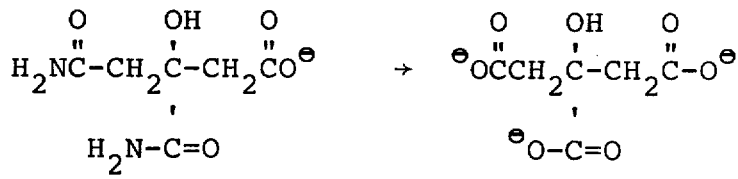

Citrate Ion

UNITED STATES PATENT OFFICE
CERTIFICATE OF CORRECTION

PATENT NO. : 3,960,941
DATED : JUNE 1, 1976
INVENTOR(S) : KARL E. WIEGAND

It is certified that error appears in the above-identified patent and that said Letters Patent are hereby corrected as shown below:

Column 14, line 17, reads -- (K(H)), -- should read -- (K(H)). --; line 24, reads -- hyroxide --, should read -- hydroxide --. Column 16, line 34, reads -- baasic --, should read -- basic --. Column 17, line 18, reads -- aslo --, should read -- also --. Column 20, line 27, reads -- 4-halobutyric or --, should read -- 4-halobutyric acid or --. Column 23, line 53, reads -- 83.7 or --, should read -- 83.7 g or --. Column 24, line 44, reads -- was required --, should read -- required --. Column 25, line 27, reads -- 90.0186 mol) --, should read -- (0.0186 mol) --. Column 27, line 17, reads -- exposide --, should read -- epoxide --. Column 28, line 52, reads -- 3,4epoxybutyric acid --, should read -- 3,4-epoxybutyric acid --.

Signed and Sealed this

Twelfth Day of October 1976

[SEAL]

Attest:

RUTH C. MASON
Attesting Officer

C. MARSHALL DANN
Commissioner of Patents and Trademarks